(12) United States Patent
Garcin et al.

(10) Patent No.: US 8,182,850 B2
(45) Date of Patent: May 22, 2012

(54) MIXTURE OF IRON AND COPPER SALTS MASKING METALLIC TASTE

(75) Inventors: Patrice Garcin, Bons en Chablais (FR); Catherine Kabaradjian, Vétraz-Monthoux (FR)

(73) Assignee: Bayer Consumer Care AG, Basel (CH)

( * ) Notice: Subject to any disclaimer, the term of this patent is extended or adjusted under 35 U.S.C. 154(b) by 982 days.

(21) Appl. No.: 12/082,521

(22) Filed: Apr. 11, 2008

(65) Prior Publication Data
US 2009/0029028 A1 Jan. 29, 2009

Related U.S. Application Data

(63) Continuation of application No. PCT/EP2006/009434, filed on Sep. 28, 2006.

(30) Foreign Application Priority Data

Oct. 11, 2005 (EP) .................................. 05292120

(51) Int. Cl.
*A23L 1/304* (2006.01)
(52) U.S. Cl. ............... 426/74; 426/72; 426/97; 426/648
(58) Field of Classification Search .................... 426/72, 426/74, 97, 648
See application file for complete search history.

(56) References Cited

U.S. PATENT DOCUMENTS

| | | | | |
|---|---|---|---|---|
| 5,211,940 A | 5/1993 | Ishiguro et al. | ................. | 424/49 |
| 5,459,162 A | 10/1995 | Saxton | .......................... | 514/499 |
| 6,368,621 B1 | 4/2002 | Engel et al. | .................... | 424/451 |
| 6,521,247 B1 | 2/2003 | deVries | ......................... | 424/439 |
| 7,585,527 B2 * | 9/2009 | Venkataraman et al. | ....... | 426/32 |
| 2005/0037065 A1 | 2/2005 | Kirschner et al. | ............. | 424/456 |
| 2005/0170014 A1 | 8/2005 | Krishnan et al. | ............. | 424/646 |
| 2008/0057162 A1 * | 3/2008 | Brucker et al. | ................. | 426/73 |
| 2011/0015150 A1 * | 1/2011 | Bortz et al. | ..................... | 514/52 |

FOREIGN PATENT DOCUMENTS

| | | |
|---|---|---|
| FR | 2085700 | 12/1971 |
| GB | 1322102 | 7/1973 |

OTHER PUBLICATIONS

Patent Abstracts of Japan vol. 013, No. 431 (C-640), Sep. 26, 1989 & JP 01 168611 A (Lion Corp), Jul. 4, 1989.
Reddy et al: "Evaluation of efficacy and safe of iron polymaltose complex and folic acid (Mumfer) vs iron formulation (ferrous fumarate) in female patients with anaemia." Journal of the Indian Medical Association, vol. 99, No. 3, 2001, pp. 154-155, XP009060053.
Morck, Timothy et al., "Inhibition of Food Iron Absorption by Coffee," Am. J. Clin. Nut. (37) pp. 416-420 (Mar. 1983).
Dallman, P.R., "Biochemical Basis for the Manifestations of Iron Deficiency," Ann. Rev. Nut. (6). pp. 13-40 (1986).
Andrews, N.C., "Disorders of the Metabolism," N.Eng.J.Med. (341) pp. 1986-1995 (1999).
Hass, J.D. et al., "Iron Deficiency and Reduced Work Capacity: a Critical Review of the Research to Determine a Causal Relationship," J.Nut. (131) p. 691S-96S (2001).
Bhaskaram, P., "Immunobiology of Mild Micronutrient Deficiencies," Brit. J. Nut. (85) pp. S75-S80 (2001).
CAS No. 7439-89-6, BP73.
Martindale 32nd Ed. 12864-h, p. 1349, Martindale 32nd Ed. P. 1339 ref 5054.
Merck Index 12th Ed. P. 4087, ref 4094.

* cited by examiner

*Primary Examiner* — Helen F Heggestad

(57) ABSTRACT

An oral composition comprising taste masked iron or copper.

9 Claims, No Drawings

MIXTURE OF IRON AND COPPER SALTS MASKING METALLIC TASTE

This application is a continuation of PCT/EP2006/009434, filed Sep. 28, 2006, which claims priority to EP 0529120.2, filed Oct. 11, 2005.

FIELD OF THE INVENTION

This invention relates to oral compositions, such as nutritional supplements or multivitamins, containing metal ions such as iron or copper. These oral compositions are formulated to mask the metallic taste. The invention also relates to processes for preparing and using the taste masked oral compositions.

BACKGROUND OF THE INVENTION

Iron is essential to most life forms and to normal human physiology. Iron is an integral part of many proteins and enzymes that maintain good health. In humans, iron is an essential component of proteins involved in oxygen transport, Dallman, P. R., "Biochemical Basis for the Manifestations of Iron Deficiency," Ann. Rev. Nut., 6, p. 13-40 (1986). Iron is also essential for the regulation of cell growth and differentiation, Andrews, N. C., "Disorders of Iron Metabolism," N. Eng. J. Med., 341, p. 1986-95 (1999). A deficiency of iron limits oxygen delivery to cells, resulting in fatigue, poor work performance, and decreased immunity, Haas, J. D., Brownlie, T., "Iron Deficiency and Reduced Work Capacity: a Critical Review of the Research to Determine a Causal Relationship," J. Nut., 131, p. 691S-6S (2001); Bhaskaram, P., "Immunobiology of Mild Micronutrient Deficiencies," Br. J. Nut., 85, p. S75-80 (2001).

Several oral compositions are known for the use as nutritional or dietary supplement containing iron. Known compositions include multivitamins and mineral supplements in various oral dosage forms that contain iron to alleviate the symptoms of iron deficiency. One drawback of most such oral supplements is that iron can give an oral dosage form a bad metallic taste. Accordingly, most such oral supplements limit the amount of iron in the formulation or use taste masking technology such as coating of iron containing granules or tablets, admixing taste masking flavors or using gelatin coated delivery systems, such as capsules or gelcaps. These approaches increase the complexity of manufacturing operation, increase the cost of the supplement, and can affect the effectiveness of the supplement, especially for persons who have difficulty swallowing tablets, capsules or gelcaps.

Other metals included in many nutritional supplements, like copper, can also impart an unpleasant metallic taste to oral supplements. Oral supplements containing copper suffer from the same drawbacks as oral supplements containing iron.

SUMMARY OF THE INVENTION

The principal object of the invention therefore is to provide an alternative oral composition containing an iron source having no metallic bad taste, or a reduced metallic bad taste, while simultaneously avoiding a complex and expensive taste masking technology.

Another object of the invention is to provide an alternative oral composition containing a copper source having no metallic bad taste, or a reduced metallic bad taste, while simultaneously avoiding a complex and expensive taste masking technology.

Yet another object of the invention is to provide an alternative oral composition containing both an iron source and a copper source having no having no metallic bad taste, or a reduced metallic bad taste, while simultaneously avoiding a complex and expensive taste masking technology.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides an oral composition having a nonmetallic taste comprising an iron source selected from the group consisting of iron polymaltose and carbonyl iron and mixtures thereof. The invention further provides a copper source that may comprise copper citrate, especially hemipentahydrate copper citrate.

Other objects and advantages of this invention will become apparent from the following descriptions and are set forth, by way of illustration and example, in certain examples set forth herein.

DETAILED DESCRIPTION OF THE INVENTION

Reference will now be made in detail to the presently preferred embodiments of the invention.

The invention comprises iron compounds salts do not cause a metallic taste when used in oral compositions. These compounds include iron salts, like iron polymaltose and substantially pure iron, such as carbonyl iron. Likewise, certain copper salts, such as copper citrate, also do not cause a metallic taste when used in oral compositions. Together these salts may be used to reduce the metallic taste of oral compositions, especially the unpleasant metallic aftertaste found in conventional oral compositions containing iron and copper.

One acceptable iron compound for use in the invention is iron polymaltose. Iron polymaltose is a water soluble macromolecular complex of polynuclear iron (III) hydroxide and partially hydrolysed dextrin (polymaltose). Iron polymaltose is a known compound described in Martindale 32nd edition, 12864-h, p. 1349.

Another compound useful in the invention is carbonyl iron. Carbonyl iron is specially purified elemental iron having a mean particle size of less than 7 µm. Carbonyl iron is known under the CAS number 7439-89-6, BP73.

Formulations in accordance with the invention may comprise from about 1 to about 60 mg of iron, preferably from about 2 to about 20 mg of iron. These ranges are based on the amount of iron in the formulation, not on the amount of iron compound in the formulation. Thus one skilled in the art would need to calculate the amount of iron in iron polymaltose to calculate the amount of iron polymaltose to use in a formulation in accordance with the invention.

An acceptable copper compound for use in accordance with the invention is copper citrate, which may comprise any kind of copper citrate solvate such as hydrates. The hemipentahydrate salt of copper citrate is preferred.

Formulations in accordance with the invention may include from about 0.1 to about 2 mg of copper, preferably from about 0.3 to about 1.1 mg copper. As with iron, one skilled in the art should calculate the amount of copper in the particular copper citrate salt selected for the formulation when determining the amount of copper citrate to use in the formulation.

The weight ratio between iron and copper in composition in accordance with the invention is from about 1:2 to about 50:1, preferably from about 5:1 to about 25:1, and most preferably from about 10:1 to about 20:1.

Composition in accordance with the invention may further comprise additional active ingredients such as vitamins and minerals. Vitamins include, but are not limited to, vitamin A, beta carotene, vitamin C (ascorbic acid), vitamin D3 (cholecalciferol), vitamin E (tocopherol acetate), vitamin B1 (thiamine), vitamin B2 (riboflavin), nicotinamide, vitamin B5 (panthothenic acid), vitamin B6 (pyridoxine), folic acid, vitamin B12 (cyanocobalamin), vitamin K1 and biotin. Acceptable minerals include, but are not limited to, calcium salts, such as calcium carbonate, calcium phosphate, or calcium glycerophosphate, magnesium salts, such as magnesium phosphate or magnesium oxide, zinc salts, such as zinc citrate; selenium salts such as sodium selenate, potassium iodide, manganese salts, such as manganese sulphate, molybdate salts such as sodium molybdate, chromium salts such as chromium chloride, sodium chloride and potassium chloride.

Compositions in accordance with the invention may also comprise iron fumarate. Preferably, the iron fumarate is in the form of microencapsulated iron fumarate. A preferred form of microencapsulation is Descote® Descote® is a trademark of Particle Dynamics, Inc. of St. Louis, Mo., used for a proprietary microencapsulation material that may be used to coat various materials. Preferred iron fumarate compositions include iron fumarate 60% Descote®. A preferred composition in accordance with the invention comprises copper citrate and iron fumarate 60% Descote® microencapsulation. Iron fumarate 60% Descote® comprises 60% iron fumarate coated with 40% mono- and di-glycerides (Merck index 12th edition, p 4087, ref 4094, Martindale 32nd edition, p. 1339 ref 5054).

The composition according to the present invention can be used as nutritional supplement or as dietary supplement for balancing the supply of iron in a patient. A patient, for the purpose of this invention, is a mammal, including a human. Compositions in accordance with the invention may be administered orally one or more times per day, preferably up to three times per day, and more preferably up to two times per day. Those skilled in the art may determine the appropriate dosage level to put into the dosage form and how many dosage forms to administer, but a typical dose would not exceed two tablets per administration. In some cases it may be advantageous to deviate from the amounts specified, depending on body weight, individual behavior toward the active ingredient, type of preparation and time or interval over which the administration is effected.

The composition according to the invention comprises suitable administration forms which deliver the compound of the invention and which include, but are not limited to, tablets, tablets which disintegrate rapidly in the oral cavity ("orodispersible" tablets), powders, sachets, granules, pellets, chewable tablets, chewing gums, dispersible tablets, effervescent compositions such as, for example, effervescent tablets or granules, liquids, solutions, emulsions, gels, syrups or drops.

Preferred dosage forms include tablets, granules, orodispersible tablets, chewable tablets, chewing gums, dispersible tablets, effervescent tablets and effervescent granules. Dosage forms are more preferably chewable tablets, orodispersible tablets, chewing gums, dispersible tablets, effervescent tablets and effervescent granules.

Formulations in accordance with the invention may further comprise ingredients that are normally used in pharmaceutical dosage forms and those that are physiologically unobjectionable such as cellulose derivatives (e.g. microcrystalline cellulose), sugars (e.g. lactose), sugar alcohols (e.g. mannitol, sorbitol), inorganic fillers (e.g. calcium phosphates), binders (e.g. polyvinylpyrrolidone, gelatin, starch derivatives and cellulose derivatives), and all other excipients necessary or appropriate to produce formulations of the desired properties, e.g. processing aids such as lubricants (magnesium stearate), disintegrants (e.g. crosslinked polyvinylpyrrolidone, sodium carboxymethylcellulose), wetting agents (e.g. sodium lauryl sulphate), release-slowing agents (e.g. cellulose derivatives, polyacrylic acid derivatives), stabilizers, sweeteners, antioxidants, preservatives, flavorings, colored pigments, and effervescent couples (preferably citric acid as acid component and sodium carbonate and/or bicarbonate as basic component).

Liquid formulations may be produced by standard methods using excipients that are usual for pharmaceuticals and nutritional supplements. Liquid formulation should contain the active ingredients in dissolved, colloidal, emulsified, or suspended form. Typical administration volumes of such liquid pharmaceutical and nutritional supplement preparations are from about 1 to about 10 ml. Examples of excipients in these liquid formulations include: solvents (e.g. water, alcohol, natural and synthetic oils, such as medium chain-link triglycerides), solubilizers (e.g. glycerol and glycol derivatives), wetting agents (e.g. polysorbate and sodium lauryl sulphate), and further excipients necessary and appropriate to produce formulations of pharmaceuticals and nutritional supplements of the desired properties such as viscosity-increasing agents, pH-correcting agents, sweeteners and flavorings, antioxidants, stabilizers, and preservatives.

Typical excipients for pharmaceuticals and nutritional supplements that are familiar to those skilled in the art may be found, for example, in the "Handbook of Pharmaceutical Excipients," Wade, A. & Weller, P. I., American Pharmaceutical Association, Washington, 2nd edition 1994.

The dosage forms may be produced by known processes. Tablets or chewable tablets may be produced by mixing and/or granulating the active ingredients together with the excipients to form a blend that is compressed to form tablets. Optionally different blends containing different ingredients and excipients can be premixed and combined to a final blend that may then be compressed to form single or multilayer tablets. With effervescent formulations the acid/base couple can be added to a final blend or the acid and the base may be added at different times to the blend to improve stability, or the base and the acid can be added to different blends that are finally combined and compressed to form single or multilayered tablets.

One advantage of the invention is that the use of complex and expensive taste masking technologies known in the prior art, such as coating of tablets or coating of granules, is not required. Gelatin coating or selection of a hard or soft gelatin capsule formulation is also not required. The composition of the present invention can be prepared by simple and less expensive procedures. Even though those skilled in the art will recognize that flavors and sweeteners may be used advantageously in the invention, especially in orodispersible tablets and liquid formulations, flavors and sweeteners are not necessary for taste masking purposes. As a result, milder flavors and less "syrupy" formulations may be used with the invention, saving costs and lessening the "medicine" taste of the formulation.

Most preferred in accordance with the invention is a fast disintegrating orodispersible tablet. For purposes of the invention, "fast" may mean that the orodispersible tablet dissolves in the mouth in about 100 seconds or less, preferably about 80 seconds or less.

EXAMPLES

Example 1

Chewable Tablets

Chewable tablets were prepared having the composition set forth in Table 1. The tablets weighed 1.230 grams each. The tablets were prepared using conventional blending and compression techniques. In table 1 and the tables that follow, "Rocoat" means Rocoat®, a trademark of Roche Vitamins Inc. of New Jersey, a subsidiary of Royal DSM NV of the Netherlands.

TABLE 1

Ingredients of Tablets of Example 1

| Active Ingredients | Amount (mg) | Form | Form Amount (mg) |
|---|---|---|---|
| Vitamin A | 400 | Vitamin A Palmitate 100,000 IU/g | 13.33 |
| Vitamin C | 30 | Ascorbic Acid | 30 |
| Vitamin D3 | 2.5 | Cholecalciferol 100,000 IU/g | 0.8 |
| Vitamin E | 5 | Tocopherol Acetate 50% CWS/S | 14 |
| Thiamin (B1) | 1.05 | Thiamin Nitrate 33% Rocoat | 3.9 |
| Riboflavin (B2) | 1.2 | Riboflavin 33% Rocoat | 3.6 |
| Nicotinamide (PP) | 13.5 | Nicotinamide | 13.5 |
| Pantothenic acid (B5) | 3 | Calcium Pantothenate | 3.26 |
| Pyridoxine (B6) | 1.5 | Pyridoxine Hydrochloride 33% Rocoat | 5.46 |
| Folic acid | 150 | Folic Acid 10% Trituration | 1.5 |
| Cyanocobalamin (B12) | 0.75 | Dry Vitamin B12 0.1% WS | 0.75 |
| Biotin | 75 | Biotin 1% Trituration | 7.5 |
| Calcium | 60 | Calcium Carbonate DCCS90L | 166.53 |
| Magnesium | 25 | Magnesium Oxide | 41.45 |
| Phosphorus | | | |
| Iron | 4 | Carbonyl Iron | 4.08 |
| Zinc | 3.75 | Zinc Citrate Trihydrate | 12.02 |
| Iodine | 37.5 | Potassium Iodide 5% Trituration | 0.75 |
| Selenium | 25 | Sodium Selenate Anhydrous 1% Trituration | 2.5 |
| Copper | 0.45 | Copper Citrate 2.5 $H_2O$ | 1.28 |
| Manganese | 0.9 | Manganese Sulfate Monohydrate | 2.77 |
| Molybdenum | 22.5 | Sodium Molybdate Dihydrate 1% Trituration | 2.25 |
| Chromium | 12.5 | Chromic Chloride Hexahydrate 1% Trituration | 1.25 |

Example 2

Chewable tablets were prepared having the composition set forth in Table 1. The tablets weighed 1.230 grams:

TABLE 2

Ingredients of Tablets of Example 2

| Active Ingredients | Amount (mg) | Form | Form Amount (mg) |
|---|---|---|---|
| Vitamin A | 400 | Vitamin A Palmitate 100000 IU/g | 13.33 |
| Vitamin C | 30 | Ascorbic Acid | 30 |
| Vitamin D3 | 2.5 | Cholecalciferol 100000 IU/g | 0.8 |
| Vitamin E | 5 | Tocopherol Acetate 50% CWS/S | 14 |
| Thiamin (B1) | 1.05 | Thiamin Nitrate 33% Rocoat | 3.9 |
| Riboflavin (B2) | 1.2 | Riboflavin 33% Rocoat | 3.6 |
| Nicotinamide (PP) | 13.5 | Nicotinamide | 13.5 |
| Pantothenic acid (B5) | 3 | Calcium Pantothenate | 3.26 |
| Pyridoxine (B6) | 1.5 | Pyridoxine Hydrochloride 33% Rocoat | 5.46 |
| Folic acid | 150 | Folic Acid 10% Trituration | 1.5 |
| Cyanocobalamin (B12) | 0.75 | Dry Vitamin B12 0.1% WS | 0.75 |

TABLE 2-continued

Ingredients of Tablets of Example 2

| Active Ingredients | Amount (mg) | Form | Form Amount (mg) |
|---|---|---|---|
| Biotin | 75 | Biotin 1% Trituration | 7.5 |
| Calcium | 60 | Calcium Carbonate DCCS90L | 166.53 |
| Magnesium | 25 | Magnesium Oxide | 41.45 |
| Phosphorus | | | |
| Iron | 4 | Iron Polymaltose | 8.8 |
| Zinc | 3.75 | Zinc Citrate Trihydrate | 12.02 |
| Iodine | 37.5 | Potassium Iodide 5% Trituration | 0.75 |
| Selenium | 25 | Sodium Selenate Anhydrous 1% Trituration | 2.5 |
| Copper | 0.45 | Copper Citrate 2.5 $H_2O$ | 1.28 |
| Manganese | 0.9 | Manganese Sulfate Monohydrate | 2.77 |
| Molybdenum | 22.5 | Sodium Molybdate Dihydrate 1% Trituration | 2.25 |
| Chromium | 12.5 | Chromic Chloride Hexahydrate 1% Trituration | 1.25 |

The following excipients may be added to the tablets of Examples 1 or 2:

TABLE 3

Excipients Used in Examples 1 and 2

| Excipients | Amount [mg] |
|---|---|
| Xylitol | 75 |
| Talc | 50 |
| Anhydrous Citric Acid | 20 |
| Magnesium Stearate | 10 |
| Orange Flavor | 10 |
| Passion Fruit Flavor | 5 |

TABLE 3-continued

Excipients Used in Examples 1 and 2

| Excipients | Amount [mg] |
|---|---|
| Aspartame | 5 |
| Sucralose | 1.5 |
| Iron Oxide | 3 |

Example 3

Effervescent tablets in accordance with invention were prepared having the active ingredients set forth in Table 4:

TABLE 4

Active Ingredients of Effervescent Tablets of Example 3

| Active Ingredients | Amount (mg) | Form | Form Amount (mg) |
|---|---|---|---|
| Vitamin A | 595 | Vitamin A Palmitate 100000 IU/g | 13.33 |
| Beta Carotene | 0.63 | Betatab 10% E | 0.63 |
| Vitamin C | 180 | Ascorbic Acid | 30 |
| Vitamin D3 | 5 | Cholecalciferol 100000 IU/g | 0.8 |
| Vitamin E | 10 | Tocopherol acetate 50% CWS/S | 14 |
| Vitamin K | 0.03 | Vitamin K1 5% SD | |
| Thiamin (B1) | 4.2 | Thiamin Phosphate | 3.9 |
| Riboflavin (B2) | 4.8 | Riboflavin Phosphate | 3.6 |
| Nicotinamide (PP) | 54 | Nicotinamide | 13.5 |
| Pantothenic Acid (B5) | 18 | Calcium Pantothenate | 3.26 |
| Pyridoxine (B6) | 6 | Pyridoxine Hydrochloride 33% Rocoat | 5.46 |
| Folic Acid | 600 | Folic Acid 10% Trituration | 1.5 |
| Cyanocobalamin (B12) | 0.003 | Dry Vitamin B12 0.1% WS | 0.75 |
| Biotin | 0.03 | Biotin 1% Trituration | 7.5 |
| Calcium | 120 | Calcium Carbonate | 71.7 |
| | | Calcium Phosphate Dibasic Anhydrous | 151.38 |
| | | Calcium Glycerophosphate | 259.86 |
| Magnesium | 45 | Magnesium Phosphate Dibasic Trihydrate | 322.81 |
| Phosphorus | 126.3 | See Calcium and Magnesium | |
| Iron | 18 | Carbonyl Iron | 18.33 |
| Zinc | 8 | Zinc Citrate Trihydrate | 25.63 |
| Iodine | 0.075 | Potassium Iodide | 0.098 |
| Selenium | 0.055 | Sodium Selenate | 0.132 |
| Copper | 0.9 | Copper Citrate | 2.57 |
| Manganese | 1.8 | Manganese Sulfate Monohydrate | 5.54 |
| Molybdenum | 0.045 | Sodium Molybdate Dihydrate | 0.113 |
| Chromium | 0.025 | Chromium Chloride Hexahydrate | 0.128 |

TABLE 4-continued

Active Ingredients of Effervescent Tablets of Example 3

| Active Ingredients | Amount (mg) | Form | Form Amount (mg) |
|---|---|---|---|
| Chloride | 39.8 | Sodium Chloride | 30 |
| Potassium | 20.4 | Potassium Chloride | 43.51 |

Example 4

Effervescent tablets in accordance with invention were prepared having the active ingredients set forth in Table 5:

TABLE 5

Active Ingredients of Effervescent Tablets of Example 4

| Active ingredients | Amount (mg) | Form | Form amount (mg) |
|---|---|---|---|
| Vitamin A | 595 | Vitamin A Palmitate 100000 IU/g | 13.33 |
| Beta Carotene | 0.63 | Betatab 10% E | 0.63 |
| Vitamin C | 180 | Ascorbic Acid | 30 |
| Vitamin D3 | 5 | Cholecalciferol 100000 IU/g | 0.8 |
| Vitamin E | 10 | Tocopherol Acetate 50% CWS/F | 14 |
| Vitamin K | 0.03 | Vitamin K1 5% SD | |
| Thiamin (B1) | 4.2 | Thiamin Phosphate | 3.9 |
| Riboflavin (B2) | 4.8 | Riboflavin Phosphate | 3.6 |
| Nicotinamide (PP) | 54 | Nicotinamide | 13.5 |
| Pantothenic acid (B5) | 18 | Calcium Pantothenate | 3.26 |
| Pyridoxine (B6) | 6 | Pyridoxine Hydrochloride 33% Rocoat | 5.46 |
| Folic acid | 600 | Folic Acid 10% Trituration | 1.5 |
| Cyanocobalamin (B12) | 0.003 | Dry Vitamin B12 0.1% WS | 0.75 |
| Biotin | 0.03 | Biotin 1% Trituration | 7.5 |
| Calcium | 120 | Calcium carbonate | 71.7 |
| | | Calcium Phosphate Dibasic Anhydrous | 151.38 |
| | | Calcium Glycerophosphate | 259.86 |
| Magnesium | 45 | Magnesium Phosphate Dibasic Trihydrate | 322.81 |
| Phosphorus | 126.3 | See Calcium and Magnesium | |
| Iron | 18 | Iron Polymaltose | 39.82 |
| Zinc | 8 | Zinc Citrate Trihydrate | 25.63 |
| Iodine | 0.075 | Potassium Iodide | 0.098 |
| Selenium | 0.055 | Sodium Selenate | 0.132 |
| Copper | 0.9 | Copper Citrate 2.5 $H_2O$ | 2.57 |
| Manganese | 1.8 | Manganese Sulfate Monohydrate | 5.54 |
| Molybdenum | 0.045 | Sodium Molybdate Dihydrate | 0.113 |
| Chromium | 0.025 | Chromium Chloride Hexahydrate | 0.128 |
| Chloride | 39.8 | Sodium Chloride | 30 |
| Potassium | 20.4 | Potassium Chloride | 43.51 |

The Excipients of Table 6 can be added to Examples 3 or 4:

TABLE 6

Excipients Used in Examples 3 and 4

| Excipients | Amount (mg) |
|---|---|
| Maltitol | qs |
| Sorbitol | qs |
| Sodium Hydrogen Carbonate | 950 |
| Anhydrous Citric Acid | 1800 |
| Sodium Carbonate | 65 |
| PVP | 30 |
| Crospovidone | 7 |
| Sucrose Ester Of Fatty Acids | 0.15 |
| Beet Red | 5 |
| Orange Flavor | 77 |
| Passion Fruit Flavor | 30 |

TABLE 6-continued

Excipients Used in Examples 3 and 4

| Excipients | Amount (mg) |
|---|---|
| Aspartame | 35 |
| Acesulfame K | 20 |

Where "qs" means the quantity needed to reach the desired tablet weight

Example 5

Orodispersible tablets in accordance with invention were prepared with the active ingredients set forth in Table 7. The tablets weighed 1000 mg:

TABLE 7

Orodispersible Tablet Active Ingredients of Example 5

| Active ingredients | Amount (mg) | Form | Form amount (mg) |
|---|---|---|---|
| Vitamin A | 400 | Vitamin A Palmitate 100000 IU/g | 13.33 |
| Vitamin C | 30 | Ascorbic Acid | 30 |
| Vitamin D3 | 2.5 | Cholecalciferol 100000 IU/g | 0.8 |
| Vitamin E | 5 | Tocopherol Acetate 50% CWS/F | 14 |
| Thiamin (B1) | 1.05 | Thiamin Nitrate 33% Rocoat | 3.9 |
| Riboflavin (B2) | 1.2 | Riboflavin 33% Rocoat | 3.6 |
| Nicotinamide (PP) | 13.5 | Nicotinamide | 13.5 |
| Pantothenic acid (B5) | 3 | Calcium Pantothenate | 3.26 |
| Pyridoxine (B6) | 1.5 | Pyridoxine Hydrochloride 33% Rocoat | 5.46 |
| Folic Acid | 150 | Folic Acid 10% Trituration | 1.5 |
| Cyanocobalamin (B12) | 0.75 | Dry Vitamin B12 0.1% WS | 0.75 |
| Biotin | 75 | Biotin 1% Trituration | 7.5 |
| Calcium | 60 | Calcium Carbonate DCCS90L | 166.53 |
| Magnesium | 25 | Magnesium Oxide | 41.45 |
| Iron | 4 | Iron Polymaltose | 8.8 |
| Zinc | 3.75 | Zinc Citrate Trihydrate | 12.02 |
| Iodine | 37.5 | Potassium Iodide 5% Trituration | 0.75 |
| Selenium | 25 | Sodium Selenate Anhydrous 1% Trituration | 2.5 |
| Copper | 0.45 | Copper Citrate 2.5 $H_2O$ | 1.28 |
| Manganese | 0.9 | Manganese Sulfate Monohydrate | 2.77 |
| Molybdenum | 22.5 | Sodium Molybdate Dihydrate 1% Trituration | 2.25 |
| Chromium | 12.5 | Chromic Chloride Hexahydrate 1% Trituration | 1.25 |
| Pharmaburst C1 | | | qs |
| Anhydrous Citric Acid | | | 16 |
| Magnesium Stearate | | | 25 |
| Sodium Hydrogencarbonate | | | 20 |
| Pineapple Flavor | | | 3 |
| Passion Fruit Flavor | | | 3 |
| Aspartame | | | 13 |
| Iron Oxide | | | 2.5 |

Example 6

Orodispersible tablets in accordance with invention were prepared having the active ingredients set forth in Table 8. The tablets weighed 1000 mg:

TABLE 8

Orodispersible Tablet Active Ingredients of Example 6

| Active ingredients | Amount (mg) | Form | Form amount (mg) |
|---|---|---|---|
| Vitamin A | 400 | Vitamin A Palmitate 100000 IU/g | 13.33 |
| Vitamin C | 30 | Ascorbic Acid | 30 |
| Vitamin D3 | 2.5 | Cholecalciferol 100000 IU/g | 0.8 |
| Vitamin E | 5 | Tocopherol Acetate 50% CWS/F | 14 |
| Thiamin (B1) | 1.05 | Thiamin Nitrate 33% Rocoat | 3.9 |
| Riboflavin (B2) | 1.2 | Riboflavin 33% Rocoat | 3.6 |
| Nicotinamide (PP) | 13.5 | Nicotinamide | 13.5 |
| Pantothenic Acid (B5) | 3 | Calcium Pantothenate | 3.26 |
| Pyridoxine (B6) | 1.5 | Pyridoxine Hydrochloride 33% Rocoat | 5.46 |
| Folic Acid | 150 | Folic Acid 10% Trituration | 1.5 |
| Cyanocobalamin (B12) | 0.75 | Dry Vitamin B12 0.1% WS | 0.75 |
| Biotin | 75 | Biotin 1% Trituration | 7.5 |
| Calcium | 60 | Calcium Carbonate DCCS90L | 166.53 |
| Magnesium | 25 | Magnesium Oxide | 41.45 |
| Iron | 4 | Iron Fumarate 60% Descote | 20.28 |
| Zinc | 3.75 | Zinc Citrate Trihydrate | 12.02 |
| Iodine | 37.5 | Potassium Iodide 5% Trituration | 0.75 |

TABLE 8-continued

Orodispersible Tablet Active Ingredients of Example 6

| Active ingredients | Amount (mg) | Form | Form amount (mg) |
|---|---|---|---|
| Selenium | 25 | Sodium Selenate Anhydrous 1% Trituration | 2.5 |
| Copper | 0.45 | Copper Citrate 2.5 H$_2$O | 1.28 |
| Manganese | 0.9 | Manganese Sulfate Monohydrate | 2.77 |
| Molybdenum | 22.5 | Sodium Molybdate Dihydrate 1% Trituration | 2.25 |
| Chromium | 12.5 | Chromic Chloride Hexahydrate 1% Trituration | 1.25 |
| Pharmaburst C1 | | | qs |
| Anhydrous Citric Acid | | | 16 |
| Magnesium Stearate | | | 25 |
| Sodium Hydrogen Carbonate | | | 20 |
| Pineapple Flavor | | | 3 |
| Passion Fruit Flavor | | | 3 |
| Aspartame | | | 13 |
| Iron Oxide | | | 2.5 |

Example 7

Manufacturing Process for Effervescent Tablets of Examples 3 and 4

The following ingredients were mixed in a drum to form a first premix: thiamine monophosphoric acid ester chloride dihydrate, riboflavin sodium phosphate, pyridoxine hydrochloride, sodium chloride and sorbitol. Not all the sorbitol shown in the table was used to make the premix. Then the following ingredients were mixed in the tank of a blender and mixed to form a second premix: the first premix, ascorbic acid, vitamin A palmitate, vitamin E powder, nicotinamide, betatab 10% E, calcium pantothenate, orange flavor, passion fruit flavor, anhydrous sodium carbonate, acesulfame potassium, aspartame, crospovidone, beet red and the remainder of the sorbitol. The second premix was then set aside.

The following ingredients were mixed to form a first pre-granulation: copper citrate 2.5H$_2$0, zinc citrate trihydrate, the iron source, manganese sulphate monohydrate, calcium carbonate, maltitol, calcium hydrogen phosphate anhydrous (a portion of the amount set forth in the table), calcium glycerophosphate, magnesium hydrogen phosphate trihydrate, sodium hydrogen carbonate and potassium chloride. The first pre-granulation was then granulated by spraying a binding solution made of purified water, sodium molybdate dihydrate, sodium selenate anhydrous, potassium iodide, ethanol, sucrose esters of fatty acids, povidone K90, and chromic chloride hexahydrate. The resulting granulation was dried, cooled and sieved to form a first granulation.

The following materials were combined in a drum: folic acid, biotin, vitamin B12, vitamin K1, vitamin D3 and sorbitol to form a third premix. In the tank of a tumble mixer the second premix, the first granulation, the third premix, and anhydrous citric acid are mixed to the final blend. The homogeneous final blend is compressed to tablets on a rotary tablet press.

Example 8

Manufacturing Process for Chewable Tablets

The following ingredients were combined in a drum and mixed for 15 minutes to form a first premix: dry vitamin D3, thiamine mononitrate, riboflavin, pyridoxine hydrochloride, folic acid, vitamin B12, calcium pantothenate, biotin, copper citrate 2.5H$_2$0, manganese sulphate monohydrate, iodine, selenium, chromium, molybdenum, orange flavor, passion fruit flavor, iron oxide yellow, aspartame, sucralose NF micronized, and pearlitol SD 200.

The first premix, vitamin A palmitate, nicotinamide, dry vitamin E, ascorbic acid, calcium carbonate, magnesium oxide heavy, iron source, zinc citrate 3H$_2$0, anhydrous citric acid, xylitol, talc, pearlitol SD 200 and sorbitol were then mixed in the drum for 20 minutes. Magnesium stearate was then added and the blend was mixed again for 5 additional minutes to form a homogenous second premix. The homogeneous second premix was then pressed to tablets on a rotary tablet press.

Example 9

Manufacturing Process for Orodispersible Tablets

The following ingredients were mixed in a drum for 15 minutes to form a first premix: dry vitamin D3, thiamine mononitrate, riboflavin, pyridoxine hydrochloride, folic acid, vitamin B12, calcium pantothenate, biotin, copper citrate 2.5H$_2$0, manganese sulphate monohydrate, iodine, selenium, chromium, molybdenum, pineapple flavor, passion fruit flavor, iron oxide yellow, aspartame and pharmaburst Cl.

The first premix, vitamin A palmitate, nicotinamide, dry vitamin E, ascorbic acid, calcium carbonate, magnesium oxide heavy, iron source, zinc citrate 3H$_2$0, anhydrous citric acid, sodium hydrogen carbonate and pharmaburst Cl were mixed for 20 minutes. Thereafter magnesium stearate was added and the final blend was mixed again for 5 additional minutes. The homogeneous final blend was compressed to form tablets on a rotary tablet press.

Example 10

Tablet for Children

Children's chewable tablets in accordance with invention were prepared having the active ingredients set forth in Table 9. The tablets weighed 1230 mg:

TABLE 9

Children's Chewable Formulation

| Active ingredients | Amount (mg) | Form | Form amount (mg) |
| --- | --- | --- | --- |
| Vitamin A | 1000 | Vitamin A Palmitate 100000 IU/g | 10 |
| Vitamin C | 22.5 | Acerola Extract 25% Vitamin C Enriched | 90 |
| Vitamin D3 | 2.5 μg | Cholecalciferol 100000 IU/g | 0.8 |
| Vitamin E | 6 | Tocopherol Acetate 50% CWS/F | 17.9 |
| Thiamin (B1) | 0.45 | Thiamin Nitrate 33% Rocoat | 1.60 |
| Riboflavin (B2) | 0.45 | Riboflavin 33% Rocoat | 1.27 |
| Nicotinamide (PP) | 6 | Nicotinamide | 6 |
| Pantothenic acid (B5) | 2 | Calcium Pantothenate | 2.17 |
| Pyridoxine (B6) | 0.45 | Pyridoxine Hydrochloride 33% Rocoat | 1.61 |
| Folic Acid | 75 μg | Folic Acid 10% Trituration | 0.75 |
| Cyanocobalamin (B12) | 1 μg | Dry Vitamin B12 0.1% WS | 1 |
| Biotin | 10 μg | Biotin 1% Trituration | 1 |
| Choline | 25 | Choline Bitartrate | 60.75 |
| Calcium | 120 | Calcium Carbonate DCCS90L | 335.30 |
| Magnesium | 25 | Magnesium Oxide | 42.89 |
| Iron | 6 | Ferrous Fumarate 60% Descote | 32.41 |
| Zinc | 4 | Zinc Citrate Trihydrate | 12.62 |
| Iodine | 60 μg | Potassium Iodide 5% Trituration | 1.137 |
| Selenium | 12.5 μg | Sodium Selenate Anhydrous 1% Trituration | 1.16 |
| Copper | 0.40 | Copper Citrate 2.5 $H_2O$ | 1.23 |
| Manganese | 1 | Manganese Sulfate Monohydrate | 3.09 |
| Chromium | 12.5 μg | Chromic Chloride Hexahydrate 1% Trituration | 1.22 |
| Mannitol | | | ca. 200 |
| Anhydrous Citric Acid | | | 20 |
| Talc | | | 50 |
| Magnesium Stearate | | | 10 |
| Xylitol | | | 75 |
| Sorbitol | | | ca. 20 |
| Cherry Flavor | | | 3 |
| Grenadine Flavor | | | 3 |
| Aspartame | | | 3 |
| Sucralose | | | 0.8 |
| Iron Oxide | | | 2.5 |

Example 11

Effervescent Tablet

Effervescent tablets in accordance with invention were prepared having the active ingredients set forth in Table 10. The tablets weighed 4800 mg:

TABLE 10

Effervescent Tablets

| Active ingredients | Amount (mg) | Form | Form amount (mg) |
| --- | --- | --- | --- |
| Vitamin A (as Retinol) | (2667.7 IU) 800 μg | Vitamin A Palmitate 100000 IU/g | (2266.7 IU) 22.67 mg |
| Vitamin A (as Beta Carotene) | (400 IU) 7.20 mg | Beta Carotene as Betatab 10% E | (400 IU) 7.20 mg |
| Vitamin D3 | (200 IU) 5 μg | Cholecalciferol Concentrate (Water Dispersible Powder Form) 100000 IU/g | 2.0 mg |
| Vitamin E | 10 mg | D-Alpha-Tocopherol Acetate Concentrate (Powder Form) 50% | 29.80 mg |
| Vitamin K | 0.03 mg | Vitamin K1 5% SD | 0.60 mg |
| Vitamin B1 | 4.20 mg | Thiamin Monophosphoric Acid Ester Chloride Dihydrate | 6.59 mg |
| Vitamin B2 | 4.80 mg | Sodium Riboflavin 5'-Phosphate | 6.56 mg |
| Niacin | 54.0 mg | Nicotinamide | 54.0 mg |
| Pantothenic acid | 18.0 mg | Calcium D-Pantothenate | 19.57 mg |
| Vitamin B6 | 6.0 mg | Pyridoxine Hydrochloride | 7.3 mg |

TABLE 10-continued

Effervescent Tablets

| Active ingredients | Amount (mg) | | Form | Form amount (mg) | |
|---|---|---|---|---|---|
| Folic acid | 0.60 | mg | Pteroylmonoglutamic Acid | 0.60 | mg |
| Vitamin B12 | 3.0 | µg | Cyanocobalamin Powder 0.1% Water Soluble | 3.0 | mg |
| Biotin | 30 | µg | Biotin | 30 | µg |
| Vitamin C | 180 | mg | Ascorbic Acid Fine Powder | 180 | mg |
| Calcium | 120 | mg | Calcium Carbonate (See Calcium Pantothenate) | 295.61 | mg |
| Magnesium | 80 | mg | Magnesium Carbonate | 163 | mg |
|  |  |  | Magnesium Sulphate Dihydrate | 159 | mg |
| Iron | 14 | mg | Ferric Pyrophosphate | 56 | mg |
| Copper | 0.9 | mg | Copper Citrate 2.5 Hydrate | 2.57 | mg |
| Iodine | 0.075 | mg | Potassium Iodine | 0.098 | mg |
| Zinc | 8 | mg | Zinc Citrate Trihydrate | 25.63 | mg |
| Manganese | 1.8 | mg | Manganese Sulphate Monohydrate | 5.54 | mg |
| Potassium | 20.4 | mg | Potassium Chloride | 38.96 | mg |
| Selenium | 50 | µg | Sodium Selenate Anhydrous | 0.12 | mg |
| Chromium | 0.025 | mg | Chromium Chloride Hexahydrate | 0.128 | mg |
| Molybdenum | 0.045 | mg | Sodium Molybdate Dihydrate | 0.113 | mg |
| Coenzyme Q10 | 3.0 | mg | Coenzyme Q10 10% | 30 | mg |

The Excipients of Table 11 can be added to Examples 10 or 11, where "qs" means the quantity added to reach the tablet weight as set forth in the example. Half the weight of mannitol SD 200 and half the weight of sorbitol may be used to obtain the theoretical tablet weight of 4800 mg. The quantity of mannitol 100 mesh may be adjusted in accordance with the desired mineral content of the tablet or granulation.

TABLE 11

Excipients Used in Examples 10 and 11

| Excipients | Amount [mg] |
|---|---|
| Mannitol 100 Mesh | qs |
| Mannitol SD 200 | qs |
| Sorbitol | qs |
| Anhydrous Citric Acid | 1800 |
| Sodium Hydrogen Carbonate | 950 |
| Orange Juice Flavor | 77 |
| Sodium Carbonate | 65 |
| Passion Fruit Flavor | 30 |
| Aspartame | 35 |
| Potassium Acesulfame | 20 |
| Crospovidone | 7 |
| Beet Red | 5 |
| Sucrose Ester of Fatty Acids | 0.15 |

Example 12

Manufacturing Process for Example 11

The following ingredients were combined in a drum to form a first premix: vitamin D3 100 CWS, biotin, folic acid, vitamin B12 0.1% WS, vitamin K1 5% SD, coenzyme Q10 10% CWS/S, sodium molybdate dihydrate, sodium selenate anhydrous and mannitol. The first premix was then mixed with the following ingredients in a blender to form a second premix: vitamin A palmitate, nicotinamide, calcium pantothenate, vitamin E powder, pyridoxine hydrochloride, riboflavin sodium phosphate, thiamin monophosphoric, betatab 10% E, crospovidone, beet red and mannitol. The second premix was then set aside.

The following ingredients were mixed to form a pre-granulation: copper citrate 2.5H$_2$0, zinc citrate trihydrate, iron source, manganese sulfate monohydrate, calcium carbonate, magnesium carbonate, magnesium sulfate dihydrate, sodium hydrogen carbonate, potassium chloride, anhydrous citric acid and mannitol. Thereafter the pre-granulation is granulated by spraying a binding solution made of ethanol, sucrose esters of fatty acids, potassium iodide and chromium chloride hexahydrate. The resulting granulation was dried, cooled and sieved.

The granule and the second premix were blended in the tank of a tumble mixer with ascorbic acid, sodium hydrogen carbonate, sorbitol, anhydrous sodium carbonate, sodium chloride, orange flavor, passion fruit flavor, potassium acesulfame, aspartame and mannitol SD 200 to form a final blend. The final blend is compressed to form tablets on a rotary tablet press.

Standard taste tests were carried out on tablets made in accordance with Examples 1 to 6, 10 and 11. The tablets did not show a metallic bad taste when administered orally. The disintegration time for the tablets of Examples 5 and 6 (the orodispersible tablets) was determined to be 67 seconds.

The purpose of the above description is to illustrate some embodiments of the present invention without implying a limitation. It will apparent to those skilled in the art that various modifications and variations may be made in the composition or procedure of the invention without departing from the scope or spirit of the invention.

What is claimed is:

1. An oral composition having a nonmetallic taste comprising (a) an iron source selected from the group consisting of iron polymaltose and carbonyl iron and mixtures thereof and (b) a copper citrate salt.

2. The oral composition of claim 1, in the form of an effervescent tablet of about 4,800 mg, wherein said iron source is about 56 mg ferric pyrophosphate and said copper citrate salt is about 2.57 mg copper citrate 2.5 hydrate and further comprising:
 (a) about 22.67 mg of vitamin A palmitate (1000,000 IU/g),
 (b) about 7.20 mg beta carotene,
 (c) about 2.0 mg cholecaliferol (water dispersible powder form 100,000 IU/g),
 (d) about 29.80 mg D-alpha-tocopherol acetate concentrate (powder form 50%),
 (e) about 0.60 mg vitamin K1 (5% SD), (f) about 6.59 mg thiamin monophosphoric acid ester chloride dehydrate,
(g) about 6.56 mg sodium riboflavin 5' phosphate,
(h) about 54.0 mg nicotinamide,
(i) about 19.57 mg calcium D-pantothenate,
(j) about 7.3 mg pyridoxine hydrochloride,
(k) about 0.60 mg pteroylmonoglutamic acid,
(l) about 3.0 mg cyanocobalamin (powder 0.1% water soluble),
(m) about 30 µg D-biotin,
(n) about 180 mg ascorbic acid (fine powder),
(o) about 295.61 mg calcium carbonate,
(p) about 163 mg magnesium carbonate,
(q) about 159 mg magnesium sulphate dihydrate,
(r) about 0.098 mg potassium iodine,
(s) about 25.63 mg zinc citrate trihydrate,
(t) about 5.54 mg manganese sulphate monohydrate,
(u) about 38.96 mg potassium chloride
(v) about 0.12 mg sodium selenate (anhydrous),
(w) about 0.128 mg chromium chloride hexahydrate,
(x) about 0.113 mg sodium molybdate dehydrate, and
(y) about 30 mg coenzyme Q10 (10%).

3. The oral composition of claim 2, wherein said copper citrate salt comprises a hemipentahydrate copper salt.

4. The oral composition of claim 2, wherein said oral composition comprises from about 1 to about 60 mg iron.

5. The oral composition of claim 2, wherein said oral composition comprises from about 0.1 to about 2 mg copper.

6. The oral composition of claim 5, wherein said oral composition comprises from about 0.3 to about 1.1 mg copper.

7. The oral composition of claim 1, further comprising iron fumarate.

8. The oral composition of claim 1, comprising a chewable tablet, an orodispersible tablet or an effervescent formulation.

9. The oral composition of claim 8, wherein said chewable tablet, orodispersible tablet or effervescent formulation has a disintegration time of less equal than 100 seconds.

* * * * *